(12) United States Patent
Kira

(10) Patent No.: US 8,293,179 B2
(45) Date of Patent: Oct. 23, 2012

(54) GAS DETECTION APPARATUS

(75) Inventor: Mitsuharu Kira, Nishinomiya (JP)

(73) Assignee: FIS Inc., Itama-shi (JP)

( * ) Notice: Subject to any disclaimer, the term of this patent is extended or adjusted under 35 U.S.C. 154(b) by 947 days.

(21) Appl. No.: 12/308,935

(22) PCT Filed: Jul. 14, 2006

(86) PCT No.: PCT/JP2006/314066
§ 371 (c)(1),
(2), (4) Date: Dec. 30, 2008

(87) PCT Pub. No.: WO2008/007438
PCT Pub. Date: Jan. 17, 2008

(65) Prior Publication Data
US 2009/0324449 A1    Dec. 31, 2009

(51) Int. Cl.
*G01N 15/06* (2006.01)
*G01N 33/00* (2006.01)
*G01N 33/48* (2006.01)
(52) U.S. Cl. ............... 422/98; 422/83; 422/94; 422/95; 422/96; 422/97
(58) Field of Classification Search ............ 422/83, 422/94, 95, 96, 97, 98
See application file for complete search history.

(56) References Cited

FOREIGN PATENT DOCUMENTS

| JP | 02-004856 | 2/1981 |
|----|-----------|--------|
| JP | 05-019101 | 2/1986 |
| JP | 63-109362 | 5/1988 |
| JP | 01-316651 | 12/1989 |
| JP | 10-090210 | 4/1998 |
| JP | 11-183422 | 7/1999 |

OTHER PUBLICATIONS

International Search Report mailed Oct. 17, 2006, issued on PCT/JP2006/314066.

*Primary Examiner* — Brian J Sines
(74) *Attorney, Agent, or Firm* — Edwards Wildman Palmer LLP

(57) ABSTRACT

A gas detection apparatus A comprises a signal processing circuit 20, a Wheatstone bridge circuit 21, integrating circuits 22 and 23, a differential amplification circuit 24, a direct current power supply circuit 25, a heater voltage application circuit 26. The Wheatstone bridge circuit 21 is configured of parallel combination of series circuits: one composed of a catalytic combustion type gas sensor 1 and a load resistor R1, and the other composed of a resistor R2, a variable resistor VR1 and a resistor R3. The heater voltage application circuit 26 is configured to generate a pulsed heater voltage by switching a direct current voltage of the direct current power supply circuit 25 through a transistor TR1 for applying the pulsed heater voltage to the Wheatstone bridge circuit 21. The integrating circuit 22 integrates a voltage at a connection point between the gas sensor 1 and the load resistor R1. The integrating circuit 23 integrates a voltage at a connection point between the variable resistor VR1 and the resistor R3. The differential amplification circuit 24 is configured to amplify a differential voltage between the output voltages of the integrating circuits 22 and 23. The signal processing circuit 20 is configured to determine a concentration of a flammable gas from an output voltage of the differential amplification circuit 24.

4 Claims, 5 Drawing Sheets

(a)

(b)

GAS DETECTION APPARATUS

TECHNICAL FIELD

The present invention relates to a gas detection apparatus for detecting a flammable gas such as hydrogen gas.

BACKGROUND

Hydrogen has attracted attention as an alternative energy source to petroleum in recent years, and the automobile equipped with a fuel cell is under development. The fuel cell vehicle is essentially equipped with a gas detection apparatus capable of detecting hydrogen gas both rapidly and accurately to detect leakage of hydrogen from the fuel cell or a hydrogen tank.

As a gas detection apparatus for detecting a flammable gas such as hydrogen gas, a catalytic combustion-type gas detection apparatus is conventionally provided with a sensing element, a voltage application unit, and a gas detection circuit. (See, for example, Japanese Unexamined Patent Application Publication No. 1998-90210) The sensing element comprises a heating unit formed of a coiled platinum wire, and a combustion unit formed into a film on the surface of the heating unit where a catalyst is dispersed. The voltage application circuit is configured to apply a heater voltage to the heating unit for heating the combustion unit by heat generated by the applied heater voltage at the heating unit. The gas detection circuit is configured to detect the flammable gas based on a change in a resistance of the heating unit (formed of the platinum wire) caused by combustion heat when a flammable gas ignites on the surface of the combustion unit.

In the catalytic combustion-type gas detection apparatus mentioned above, platinum is generally utilized as materials of the heating unit and a resistance-temperature detector. The platinum has a resistance of several ohms ($\Omega$) to several tens of ohms ($\Omega$). The heater voltage is set to be applied to the heater unit at about 0.2 V to 2 V so as to attain a sufficient detection voltage while saving electrical power consumption.

Since the voltage of the battery installed in the vehicle is 12 V or 24 V, the circuit voltage of the gas detection apparatus is set at 5 V or 12 V in use of the catalytic combustion-type gas detection apparatus installed on a fuel cell vehicle. For generation of the heater voltage (about 0.2 V to 2 V) to be supplied to the heating unit by the voltage application circuit, the circuit voltage of 5 V or 12 V needs to be stepped down by a series regulator or a switching regulator circuit. The step-down of the voltage by the series regulator causes a problem of wasteful use of electrical power by control elements and resistors comprising the series regulator circuit. In addition, the switching regulator circuit necessitates a complex circuit configuration having a large number of components as well as a large space for mounting thereon an inductor, being responsible for mounting cost of the apparatus.

The gas detection apparatus installed on the fuel cell vehicle is configured to stop the engine, depending on its detection result. In order to ensure sufficient safety while preventing engine shutdowns due to detection errors, the gas detection apparatus needs to detect hydrogen gas with high accuracy in a short time, for reducing electrical power consumption without badly affecting its ability to detect the hydrogen gas.

DISCLOSURE OF THE INVENTION

In view of the above problem, the present invention has been accomplished and has an object of providing a low-cost gas detection apparatus reducing electrical power consumption.

In order to achieve this object, the present invention according to claim 1 comprises a gas sensing unit having a detection resistor and an igniter. The detection resistor is heated by Joule heat in the presence of electric current flowing therethrough. The igniter is configured to ignite a flammable gas by a catalytic action as a result of being heated by the heat of the detection resistor. The present invention also includes a load resistor connected in series to the detection resistor, a heater voltage application circuit, and a gas detection circuit. The heater voltage application circuit is configured to apply a pulsed heater voltage having a cycle shorter than a thermal time constant of the gas sensing unit across a series circuit composed of the detection resistor and the load resistor. The gas detection circuit is configured to provide an output signal of the gas sensing unit from a voltage obtained by integrating a voltage at a connection point between the detection resistor and the load resistor.

According to this invention, the heater voltage application circuit is configured to apply the pulsed heater voltage having the cycle shorter than the thermal time constant of the gas sensing unit across the series circuit composed of the detection resistor and the load resistor, for supplying the detection resistor with a predetermined voltage to heat the detection resistor up to a specific temperature. This configuration does not necessitate any circuit for stepping down a power supply voltage to a mean voltage applied to the detection resistor, not requiring the use of electrical power for the step-down of the power supply voltage, thereby enabling to provide the gas detection apparatus reducing electrical power consumption. Moreover, this configuration does not require any complex circuit such as a switching regulator circuit for generating a voltage applied to the detection resistor, enabling to reduce the cost of the gas detection apparatus as well as minimize space for mounting thereon, thereby providing a compact gas detection apparatus. When being applied to the detection resistor, the pulsed heater voltage generates a pulsed voltage across the detection resistor. Since the generated pulsed voltage slightly varies its peak voltage in response to a concentration of the flammable gas, the heater voltage needs to be applied in a short cycle for stabilizing a temperature of the heated detection resistor, necessitating an expensive amplifier having a rapid response rate because ordinary amplifiers are unable to follow the variation of the voltage across the detection resistor. In contrast, the present invention according to claim 1 utilizes the integrated voltage obtained by an integrating circuit as the output signal of the gas sensing unit, not requiring any expensive element having a rapid response rate for determination of the gas concentration by the output signal, thereby enabling to utilize inexpensive components for configuring the gas detection circuit.

The present invention according to claim 2 comprises the gas sensing unit having the detection resistor and the igniter. The detection resistor is heated by Joule heat in the presence of the electric current flowing therethrough. The igniter is configured to ignite the flammable gas by the catalytic action as a result of being heated by the heat of the detection resistor. The present invention according to claim 2 also includes a reference resistor, the heater voltage application circuit, and the gas detection circuit. The reference resistor is formed to the same shape and dimensions from the same material as the detection resistor, and is designed to be deactivated by the flammable gas. The heater voltage application circuit is configured to apply the pulsed heater voltage having the cycle shorter than the thermal time constant of the gas sensing unit across the series circuit composed of the detection resistor and the reference resistor. The gas detection circuit is configured to provide the output signal of the gas sensing unit from a voltage obtained by integrating a voltage at a connection point between the detection resistor and the reference resistor.

According to this invention, the heater voltage application circuit is configured to apply the pulsed heater voltage having the cycle shorter than the thermal time constant of the gas sensing unit across the series circuit composed of the detection resistor and the reference resistor, for supplying the detection resistor and the reference resistor with a predetermined voltage to heat the detection resistor and the reference resistor up to a specific temperature. This configuration does not necessitate any circuit for stepping down a power supply voltage to a mean voltage applied to the detection resistor and the reference resistor, not requiring the use of electrical power for the step-down of the power supply voltage, thereby enabling to provide the gas detection apparatus reducing electrical power consumption. Moreover, this configuration does not require any complex circuit such as a switching regulator circuit for generating a voltage applied to the detection resistor and the reference resistor, enabling to reduce the cost of the gas detection apparatus as well as minimize space for mounting thereon, thereby providing the compact gas detection apparatus. When being applied to the detection resistor and the reference resistor, the pulsed heater voltage generates a pulsed voltage across the detection resistor and the reference resistor. Since the generated pulsed voltage slightly varies its peak voltage in response to the concentration of the flammable gas, the heater voltage needs to be applied in a short cycle for stabilizing temperature of the heated detection resistor and the heated reference resistor, necessitating the expensive amplifier having the rapid response rate because ordinary amplifiers are unable to follow the variation of the voltage across the detection resistor. In contrast, the present invention according to claim 2 utilizes the integrated voltage obtained by the integrating circuit as the output signal of the gas sensing unit, not requiring any expensive element having the rapid response rate for determination of the gas concentration by the output signal, thereby enabling to utilize inexpensive components for configuring the gas detection circuit.

The present invention according to claim 3 is the gas detection apparatus as set forth in claim 1 or claim 2, wherein the gas detection circuit comprises an integrating circuit unit composed of a resistor and a capacitor for integrating and smoothing the voltage at the connection point and an amplification circuit unit for amplifying the voltage smoothed by the integrating circuit unit to provide the output signal of the gas sensing unit.

The gas detection apparatus of this invention outputs the voltage, which is integrated by the integrating circuit unit and then amplified by the amplification circuit unit, as the output signal of the gas sensing unit, increasing the output signal level of the gas sensing unit, and thereby enabling to detect the gas with high resolution and accuracy.

The present invention is the gas detection apparatus as set forth in claim 1 or claim 2, comprising a bridge circuit configured by a series connection of a plurality of bridge resistors between both ends of the series circuit. The gas detection circuit of the present invention also comprises a first integrating circuit unit for integrating the voltage at the connection point, a second integrating circuit unit for integrating a voltage at a connection point between the bridge resistors, and a differential amplification circuit unit for amplifying a differential voltage between output voltages of both integrating circuit units to provide the output signal of the gas sensing unit.

According to this invention, the bridge circuit is configured by the series connection of a plurality of the bridge resistors between both ends of the series circuit composed of the detection resistor and the reference resistor. The gas detection apparatus in the present invention integrates the voltage at the connection point between the detection resistor and the reference resistor by the first integrating circuit unit as well as the voltage at the connection point between the bridge resistors by the second integrating circuit unit, and then amplifies the differential voltage between the output voltages of both integrating circuit units by the differential amplification circuit unit. With the use of the bridge circuit, the gas detection apparatus of the present invention gives a large output indicative of voltage changes at the connection point between the detection resistor and the reference resistor by the differential amplification circuit unit, thereby enabling to detect the gas with high resolution and accuracy.

The present invention is the gas detection apparatus as set forth in claim 1 or claim 2, wherein the gas detection circuit comprises a sampling circuit unit for sampling the output signal of the gas sensing unit at predetermined intervals for detecting the flammable gas based on the sampled output signal.

This invention enables to detect the flammable gas based on the output signal which is sampled by the sampling circuit unit from the output signal of the gas sensing unit at predetermined intervals during the application of the pulsed heater voltage or thereafter.

BEST MODE FOR CARRYING OUT THE INVENTION

Hereafter, a gas detection apparatus of the present invention will be described with reference to preferred embodiments in detail.

First Embodiment

Figure 3:
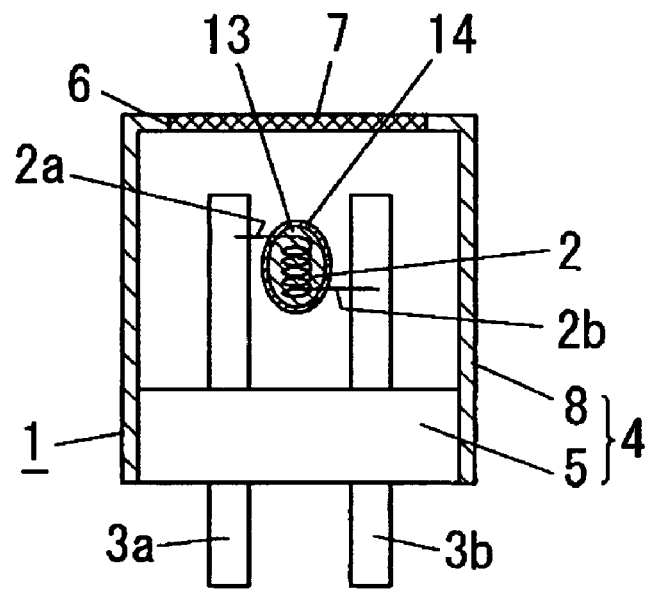
FIG. 3(a) is a cross-sectional view and FIG. 3(b) is an external perspective view showing a gas sensor used for the gas detection apparatus in the above embodiment.
Figure 3:
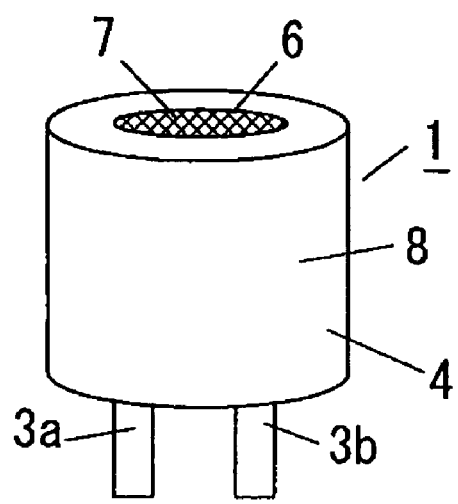

FIG. 3(a) and 3(b) are respectively a cross-sectional view and an external perspective view of a gas sensor 1 used in the gas detection apparatus of the present embodiment. This gas sensor 1 comprises a heating resistor 2, lead terminals 3a and 3b, and a sensor receptacle 4 composed of a base 5 and a protective cap 8.

The heating resistor 2 is configured to act as both an igniter and a detection resistor. The igniter ignites a flammable gas (for example, hydrogen gas in the present embodiment) adsorbed on a surface thereof by a catalytic action. The detection resistor heats the igniter up to a temperature of 80° C. to 450° C. by Joule heat generated by application of an electric current therethrough when a flammable gas is not ignited on the surface of the igniter.(i.e. in the absence of the temperature rise due to catalytic combustion). The detection resistor changes its resistance in response to a temperature rise by combustion heat generated by the catalytic combustion of the flammable gas. Namely, the heating resistor 2 comprises the detection resistor and the igniter, so as to constitute a gas sensing unit.

The heating resistor 2 is formed of a coiled platinum wire (e.g. a coiled platinum wire having a wire diameter of about 10 to 50 µm), and both ends thereof are electrically and mechanically connected to the lead terminals 3a and 3b on both sides. In the present embodiment, the heating resistor 2 is formed into 5 to 15-turn coil with a coiled diameter of about 100 to 500 µm, an interval between adjacent wires of about 20 µm. An inorganic porous thermal insulator 13 is formed into a bead-shaped at the coiled portion of the heating resistor 2 by coating and baking of alumina sol or silica sol made as a binder from fine powder of alumina or silica. In addition, a silicone trap layer 14 is formed of an activated charcoal supported with platinum, or made by an addition of platinum to a product resulting from coating and baking of the aluminum sol or silica sol, so as to cover the surface of the inorganic porous thermal insulator 13. Although being formed around the thermal insulator 13 in the present embodiment, the silicone trap layer 14 may be formed directly on the coiled portion of the heating resistor 2 without supply of the thermal insulator 13.

The present invention inhibits silicone poisoning by the silicone trap layer 14 adsorbing thereon the silicone. As being protected by the thermal insulator 13 interposed between the silicone trap layer 14 and the heating resistor 2, the silicone trap layer 14 is not heated by the heat conducted from the heating resistor 2 up to the high temperature causing thereon the catalytic combustion, thereby being kept well, and enabling to pass therethrough the gas to induce the catalytic combustion of the flammable gas (hydrogen gas) on the surface of the heating resistor 2. Although acting as both of the igniter and the detection resistor in the present embodiment, the heating resistor 2 may be formed into coiled-shape, and then buried within an igniter (not shown) made of the bead-shaped inorganic porous body supporting therein a precious metal catalyst such as platinum, so as to merely act as a detection resistor. The silicone trap layer may be provided to the surface of the igniter with an inorganic porous thermal insulating layer interposed therebetween so as to prevent the silicone poisoning.

The base 5 is formed of a synthetic resin in the shape of a disc. The two lead terminals 3a and 3b are provided to the base 5 so as to pass therethrough in the vertical direction, and both ends 2a and 2b of the heating resistor 2 are respectively attached firmly to upper portions of the lead terminals 3a and 3b protruding from the upper surface of the base 5 by soldering or the like.

The protective cap 8 is formed into a cylinder-like shape having an opening at its bottom where the base 5 is firmly inserted, so as to accommodate therein the heating resistor 2. A round ventilation hole 6 is provided at the center of upper surface of the protective cap 8, and covered with a 100 mesh stainless steel screen 7 for having explosion proof. The protective cap 8 may be made of a metal or a plastic.

Figure 4:
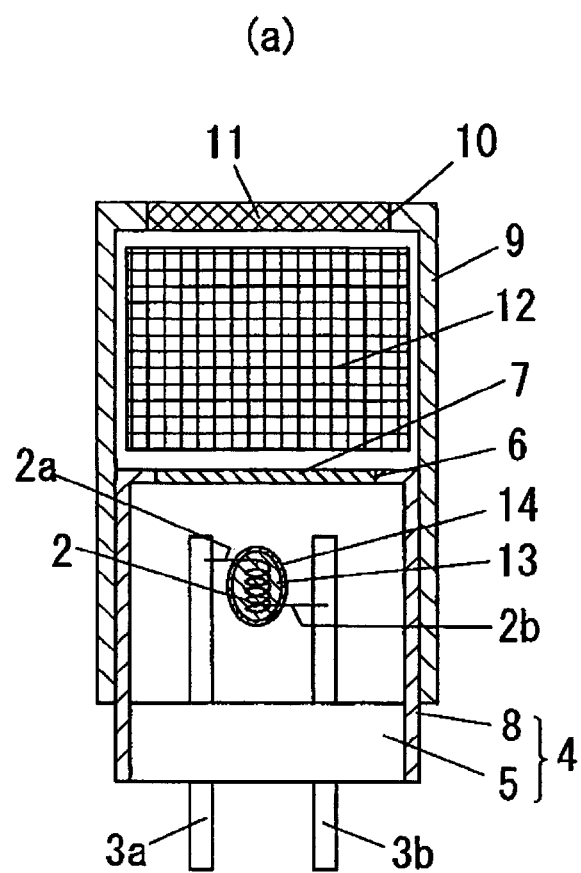
FIG. 4(a) is a cross-sectional view and FIG. 4(b) is an external perspective view showing a gas sensor with a filter cap used for the gas detection apparatus in the above embodiment.
Figure 4:
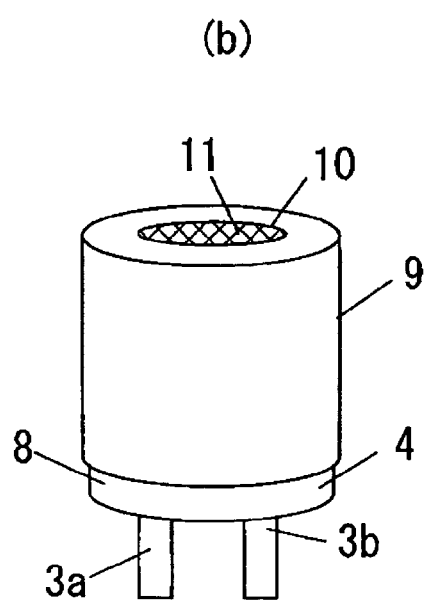

As shown in FIGS. 4(*a*) and 4(*b*), a filter cap 9 carrying therein a filter 12 is preferably disposed over the top of the protective cap 8 to further suppress the silicone poisoning by silicone in the atmosphere. The filter cap 9 is made of a synthetic resin and is formed into a cylinder-like shape closed at its upper end. A gas inlet port 10 is formed in the shape of a round at the upper surface of the filter cap 9, and covered with a 100 mesh stainless steel screen 11 attached to the periphery thereof for having explosion proof. The filter 12 is attached to inside of the filter cap 9 for adsorbing poisonous substances in gas passing through the gas inlet port 10. This filter 12 is made of an adsorbent porous member (such as active carbon, silica gel, zeolite), or an adsorptive material comprising an organic or inorganic porous body impregnated with a chemical substance capturing liquid, for adsorbing thereon poisonous substances (such as silicon) in the gas so as to suppress the poisoning of the heating resistor 2 and thereby keep well sensitivity thereof. The chemical substance capturing liquid may be KOH for removing oxidative gases, or phosphoric acid for removing ammonia, amines and the like. The organic or inorganic porous body may be impregnated with a liquid component suitable for adsorbing thereon specific poisonous substances.

Figure 1:
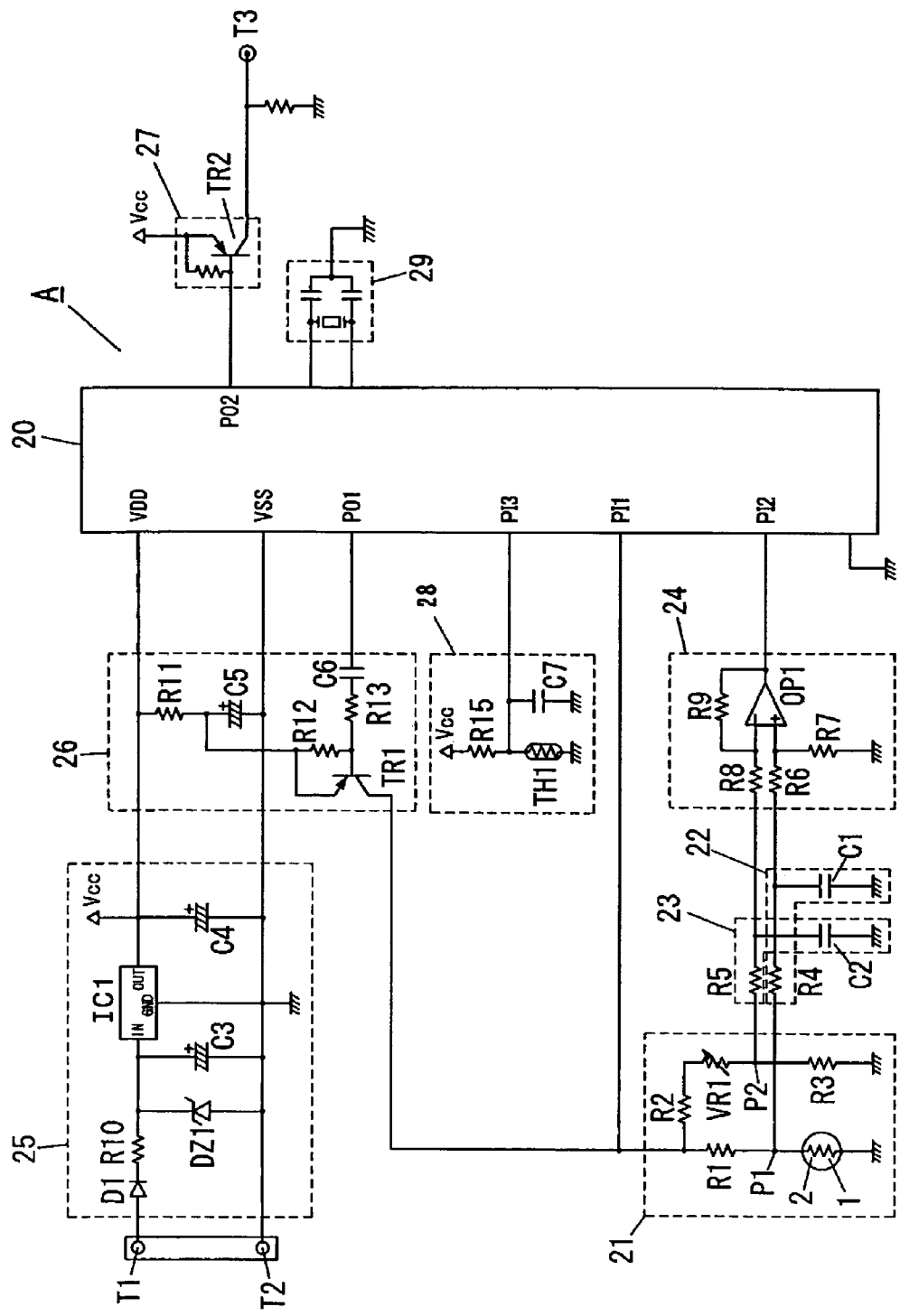
FIG. 1 is a circuit diagram of a gas detection apparatus in accordance with a first embodiment.

Next, a circuit configuration of the gas detection apparatus A is described based on the circuit diagram of FIG. 1. The gas detection apparatus A mainly comprises a signal processing circuit 20 (composed of a microcomputer or the like), a Wheatstone bridge circuit 21, integrating circuits 22 and 23, a differential amplification circuit 24, a direct current power supply circuit 25, a heater voltage application circuit 26, an output circuit 27, a temperature compensation circuit 28, and a clock circuit 29 providing a clock signal to the signal processing circuit 20. The direct current power supply circuit 25 acts as electric sources of the signal processing circuit 20 and so on.

The Wheatstone bridge circuit 21 is comprised of series circuits combined with each other in parallel. One of the series circuits comprises the gas sensor 1 (namely, the heating resistor 2) and a load resistor R1, and the other includes a resistor R2, a variable resistor VR1 and a resistor R3.

The integrating circuit 22 (first integrating circuit unit) is comprised of a CR circuit including a resistor R4 and a capacitor C1 connected in series between a connection point P1 and its circuit ground, so as to generate a voltage obtained by integration of a voltage at the connection point P1. The integrating circuit 23 (second integrating circuit unit) is comprised of a CR circuit including a resistor R5 and a capacitor C2 connected in series between a connection point P2 and its circuit ground, for generating a voltage obtained by integration of a voltage at the connection point P2. In this embodiment, the resistances of the resistors R4 and R5 are respectively selected to have resistant values of e.g. 20 k$\Omega$, and the capacitors C1 and C2 are selected to have the electrostatic capacitances of e.g. 0.1µF. The time constants of the integrating circuits 22 and 23 are selected at about 2 msec.

The differential amplification circuit 24 is a conventionally known circuit comprised of an operational amplifier OP1 and resistors R6 to R9. The non-inverting input terminal of the operational amplifier OP1 is connected via the resistor R6 to a connection point between the resistor R4 and the capacitor C1, and also connected to the circuit ground via the resistor R7. The inverting input terminal of the operational amplifier OP1 is connected via the resistor R8 to a connection point between the resistor R5 and the capacitor C2, and also connected to its output terminal via the resistor R9. Thus, the operational amplifier OP1 amplifies a differential voltage between the output voltages of the integrating circuit 22 and the integrating circuit 23 (between voltage across the capacitor C1 and voltage across the capacitor C2) in a predetermined gain, and then feed the amplified voltage to an input terminal PI2 of the signal processing circuit 20.

The direct current power supply circuit 25 comprises a series circuit including a resistor R10 and a Zener diode DZ1 which are connected in series to a diode D1, between terminals T1 and T2 which are connected to an external power supply. The direct current power supply circuit 25 also comprises a capacitor C3 connected in parallel with the Zener diode DZ1, and a three-terminal regulator IC1. The three-terminal regulator IC1 has its input side connected to the capacitor C3 and its output side connected to a capacitor C4. After being supplied with a direct current voltage (for example, DC 12 V) via the terminals T1 and T2 from a battery or other external power supply, the direct current power supply circuit 25 steps down the direct current voltage by the Zener diode DZ1, then stabilize the resultant voltage, and subsequently convert into a direct current voltage Vcc (for example, DC 5 V) by the three-terminal regulator IC1 to be output to the heater voltage application circuit.

The heater voltage application circuit 26 comprises a series circuit including a resistor R11 and a capacitor C5 which are respectively connected to output terminals of the direct current power supply circuit 25. The heater voltage application circuit 26 also comprises a pnp transistor TR1 having its emitter connected to a connection point between the resistor R11 and the capacitor C5, its collector connected to a high-voltage input terminal of the Wheatstone bridge circuit 21 (in other words, a connection point between the resistors R1 and R2), and its base connected to its emitter via a resistor R12 as well as connected to an output terminal PO1 of the signal processing circuit 20 via a series circuit composed of a resistor R13 and a capacitor C6. The signal processing circuit 20 turns on the transistor TR1 to supply the direct current voltage to the Wheatstone bridge circuit 21 in the case of a low-level (L-level) voltage at its output terminal PO1, while it turns off the transistor TR1 so as to stop the supply in the case of a high-level (H-level) voltage. Thus, by control of the voltage at output terminal PO1 in the high or low level, the signal processing circuit 20 achieves on-off switch of the transistor TR1 for regulating the output voltage of the direct current power supply circuit 25 supplied to the Wheatstone bridge circuit 21 in a predetermined pulse width. The signal processing circuit 20 has its input terminal PI1 to receive a voltage of the high-voltage input terminal of the Wheatstone bridge circuit 21, enabling to monitor the voltage fed to its input terminal PI1 after the application of the pulsed voltage by the heater voltage application circuit 26, for detecting disconnection of the heating resistor 2. Namely, in the case of H-level of the input terminal PI1 while the transistor TR1 being off after the application of the pulsed voltage, the signal processing circuit 20 detects the disconnection between the load resistor R1 and the ground via the heating resistor R2.

The output circuit 27 has a pnp transistor TR2 with a resistor connected between its base and its emitter. The transistor TR2 has its emitter receiving a voltage Vcc, its collector connected to a circuit ground via a resistor, and its base connected to an output terminal PO2 of the signal processing circuit 20 so as to achieve on-off switch thereof in response to an output signal from the signal processing circuit 20, for outputting a serial signal from a terminal T3 connected to its collector.

The temperature compensation circuit 28 is comprised of a series circuit including a thermistor TH1 and a resistor R15 for receiving a direct current voltage Vcc. The temperature compensation circuit 28 also comprises a capacitor C7 connected in parallel with the thermistor TH1. The voltage across the thermistor TH1 is fed to an input terminal PI3 of the signal processing circuit 20.

Figure 2:
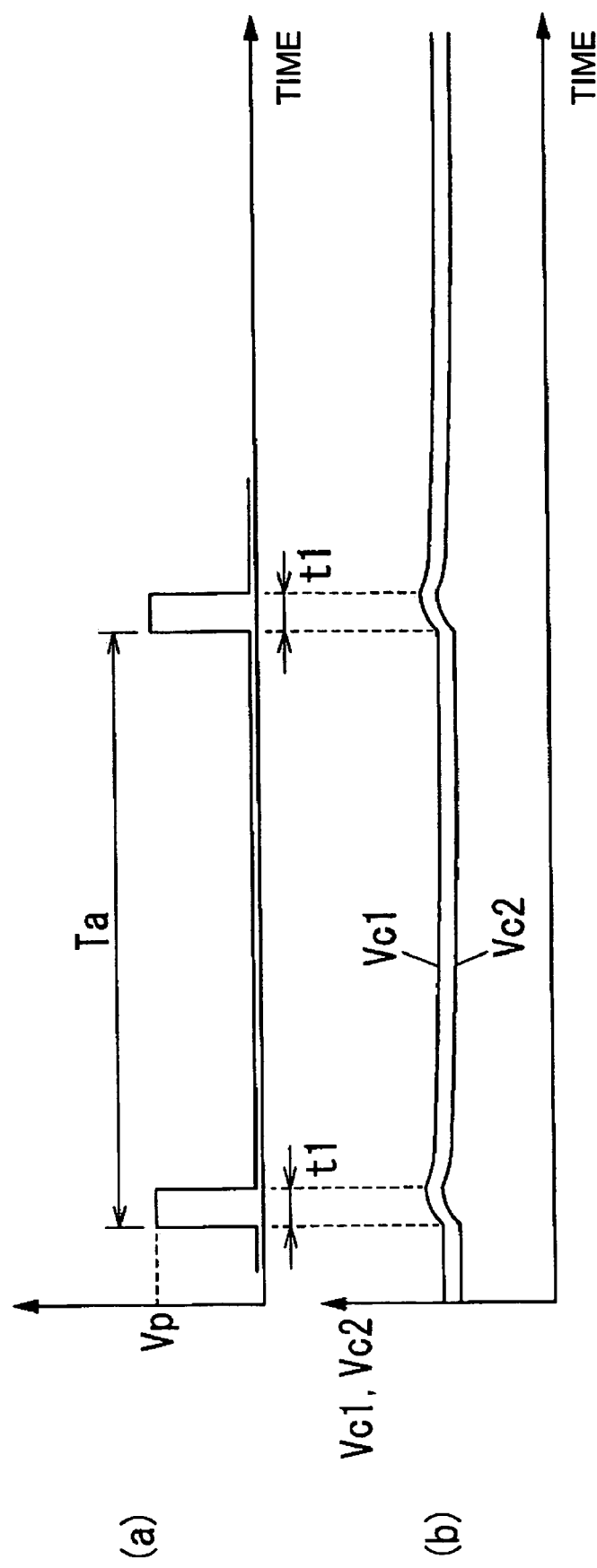
FIGS. 2(a) and 2(b) are timing charts for explaining the operation of the gas detection apparatus in the above embodiment.

Next, an operation of the gas detection apparatus A is described based on FIG. 2. FIG. 2(a) is a waveform diagram of a pulsed voltage applied to the Wheatstone bridge circuit 21. FIG. 2(b) is a waveform diagram showing output voltages Vc1 and Vc2 of the integrating circuits 22 and 23.

In the Wheatstone bridge circuit 21, the resistance of the variable resistor VR1 is selected so as to nearly coincide the voltage at the connection point P1 between the gas sensor 1 and the load resistor R1 with that at the connection point P2 between the variable resistor VR1 and the resistor R3 in the absence of any flammable gas in the atmosphere. Thus, the output of the integrating circuit 22 is nearly equal to that of the integrating circuit 23, and the output voltage of the differential amplification circuit 24 is almost zero in the absence of any flammable gas in the atmosphere.

The signal processing circuit 20 controls the voltage of the output terminal PO1 in the L level with a predetermined time width at intervals of a predetermined pulse cycle Ta (e.g., 4 msec) to turn on the transistor TR1 at the time, for applying a pulsed voltage having a predetermined pulse width t1 (e.g., about 160 μsec) and a constant amplitude Vp (e.g. about 4.5 V) from the heater voltage application circuit 26 to the Wheatstone bridge circuit 21 (see FIG. 2(a)) so as to heat up the heating resistor 2 of the gas sensor 1 at a specific temperature. The applied pulsed voltage has a sufficiently short cycle, thereby igniting the detection resistor 2 of the gas sensor 1 at a constant temperature.

In the presence of the flammable gas in the atmosphere, the flammable gas ignites on the surface of the heating resistor 2, varying the resistance of the heating resistor 2 due to the combustion heat. The vary of the resistance changes the voltage at the connection point P1 between the load resistor R1 and the gas sensor 1 as shown in FIG. 2(b), and then changes the output Vc1 of the integrating circuit 22, and thus changes the output of the differential amplification circuit 24 in accordance with the change in the output of the integrating circuit 22 (in other words, the differential voltage between the output voltages Vc1 and Vc2 of the integrating circuits 22 and 23).

The signal processing circuit 20 is configured to sample the voltage of the input terminal PI2 (in other words, the output voltage of the differential amplification circuit 24) at predetermined intervals after the pulsed voltage is applied to the Wheatstone bridge circuit 21 by the heater voltage application circuit 26. The signal processing circuit 20 is provided with an internal memory (not shown) to store therein a calibration curve data showing the relationship between the input voltage at the input terminal PI2 and a concentration of a target gas, enabling to calculate the concentration of the flammable gas by use of the sampled voltage, based on the calibration curve data stored in the internal memory. After completing the calculation of gas concentration, the signal processing circuit 20 controls the voltage level of the output terminal PO2 in high or low-level so as to turn the transistor TR2 on or off for outputting the measurement result as a serial data from the output terminal T3. The signal processing circuit 20 may be configured to output the calculated result of gas concentration as an analog voltage value using a D/A converter, or the measurement result in any type of signal. As being capable of detecting atmospheric temperature from the input voltage of the input terminal PI3, the signal processing circuit 20 may be configured to carry out temperature compensation of the measurement result based on the detection result of atmospheric temperature. In this embodiment, a sampling circuit unit is composed of the signal processing circuit 20, and a gas detection circuit comprises the signal processing circuit 20, the integrating circuits 22 and 23, and the differential amplification circuit 24 serving as an amplification circuit unit.

As described above, the heater voltage application circuit 26 is configured to apply a pulsed heater voltage having a cycle shorter than a thermal time constant of the heating resistor 2 acting as the gas sensing unit across the series circuit composed of the heating resistor 2 (the gas sensor 1) and the load resistor R1, for supplying the heating resistor 2 with a predetermined electric power to heat the heating resistor 2 up to a specific temperature in the present embodiment. This configuration does not necessitate any circuit for stepping down a power supply voltage to a mean voltage applied to the heating resistor 2, not requiring the use of the electrical power for the step-down of the power supply voltage. Being provided with the integrating circuit composed of the resistor R11 and the capacitor C5, the heater voltage application circuit 26 averages current consumption of the three-terminal regulator IC1, considerably reducing the current consumption of the three-terminal regulator IC1, and thereby enabling to provide the gas detection apparatus reducing electrical power consumption, compared to the use of a series regulator for stepping down the output voltage of the three-terminal regulator IC1 voltage to be applied to the Wheatstone bridge circuit 21 instead of the use of the heater voltage application circuit 26. Moreover, this configuration does not require any complex circuit such as a switching regulator circuit for generating the voltage applied to the heating resistor 2, enabling to reduce the cost of the gas detection apparatus A. The thermal time constant of the gas sensing unit (the heating resistor 2) varies between ca. 50 and 300 msec depending on the type thereof, and is about 100 msec in the present embodiment. The cycle of the heater voltage is selected to be preferably 10% or less, and more preferably 5% or less (for example, 4 msec in the present embodiment) of the thermal time constant of the gas sensing unit, for keeping nearly constant the temperature of the gas sensing unit while reducing power consumption thereof. For the limitation on the arithmetic processing speed of the microcontroller, the lower limit on the cycle of the heater voltage is at least 1% of the thermal time constant, and thereby the cycle of the heater voltage is preferably selected to be 1% to 10%, more preferably 1% to 5% of the thermal time constant of the gas sensing unit.

When being applied to the heating resistor 2 by the heater voltage application circuit 26, the pulsed heater voltage generates a pulsed voltage across the heating resistor 2. The generated pulsed voltage slightly varies its peak voltage in response to the concentration of the flammable gas, requiring the period Ta of the pulsed heater voltage to be shortened so as to stabilize temperature of the heated heating resistor 2, and thereby necessitating an expensive amplifier having a rapid response rate because ordinary inexpensive amplifiers are hardly capable of amplifying the slight variation of the peak voltage for being output. In contrast, the gas detection apparatus in the present embodiment enables to utilize inexpensive components for configuring a gas detection circuit, not requiring any expensive element having a rapid response rate for determination of gas concentration by the output signal. The time constants of the integrating circuits 22 and 23 are suitably selected in consideration of the pulse width and measurement cycle (pulse cycle) of the heater voltage, such that the gas detection apparatus can sufficiently smooth the generated pulsed voltage across the heating resistor 2 and minimize a response delay after the application of the pulsed heater voltage across the heating resistor 2 to reduce a time for detection of the flammable gas, and be manufactured by inexpensive components such as ceramic capacitors. In the present embodiment, the time constants of the integrating circuits 22 and 23 are selected to be 2 msec.

In addition, the gas detection apparatus in the present embodiment smoothes a voltage at the connection point between the load resistor R1 and the gas sensor 1 by the integrating circuit 22, and then amplifies the differential voltage between the output voltages of the integrating circuits 22 and 23 by the differential amplification circuit 24 so as to provide an output signal of the gas sensing unit. This configuration enables to increase the output signal level of the gas sensing unit, thereby detecting the gas with high resolution and accuracy.

During or just after the application of the pulsed heater voltage by the heater voltage application circuit 26, the voltage at the connection point P1 is incompletely smoothed by the integrating circuit 22. When using the voltage, the signal processing circuit 20 may increase the measurement error in sampling the output of the differential amplification circuit 24 for calculating the concentration of the flammable gas. In view of this problem, the signal processing circuit 20 is configured to sample the output signal of the gas sensing unit (i.e., the output signal of the differential amplification circuit 24) at intervals of a predetermined time (for example, 1 msec) after the application of the pulsed heater voltage by the heater voltage application circuit 26, and then detect the flammable gas based on the sampled output signal in the present embodiment. This configuration reduces the measurement error, enabling to rapidly conduct the measurement with satisfactory reproducibility.

The signal processing circuit 20 serving as the sampling circuit unit may sample the output of the integrating circuit 22 during application of the pulsed heater voltage. The integrating circuit 22 provides a higher output level during application of the heater voltage than that after the application, minimizing the detection error. When the sampling is carried out at intervals of a constant time, the gas concentration is proportional to the output of the integrating circuit 22. The signal processing circuit 20 can be configured to detect the flammable gas in preparation of a calibration curve data for the output voltage sampled at the time intervals, even when sampling the output of the integrating circuit 22 during the application of the heater voltage.

Second Embodiment

Figure 5:
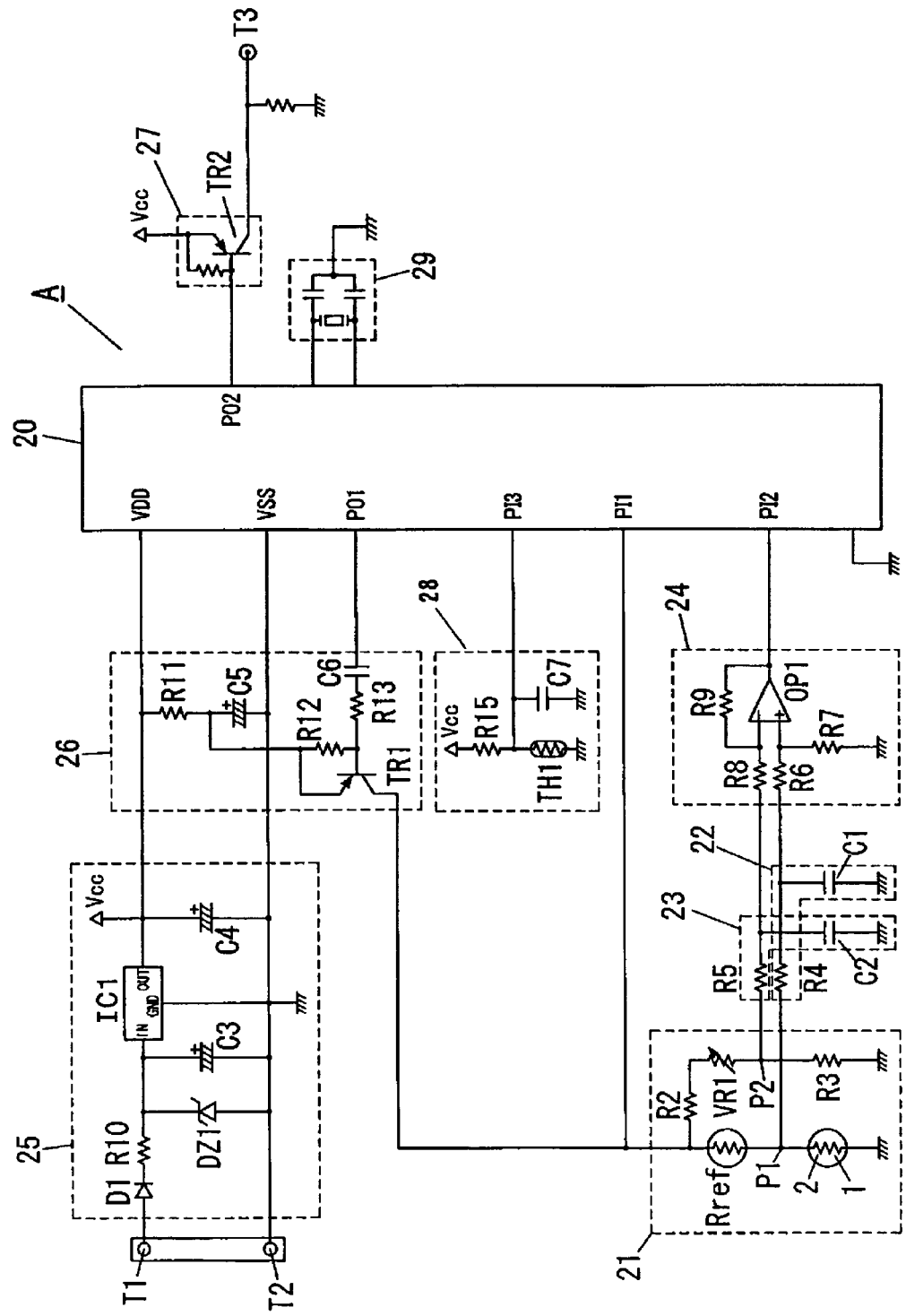
FIG. 5 is a circuit diagram of a gas detection apparatus in accordance with a second embodiment.

Hereafter, a second embodiment of the present invention is described based on FIG. 5. In contrast to the abovementioned first embodiment where the load resistor R1 is connected in series with the gas sensor 1, the present embodiment utilizes a reference resistor Rref, instead of the load resistor R1. The reference resistor Rref is formed to the same shape and dimensions from the same material as the heating resistor 2, and designed to be deactivated by the flammable gas. The present configuration in this embodiment is consistent with that of first embodiment, except for the reference resistor Rref. Like parts are designated by like reference numerals, and no duplicate explanation deemed necessary.

The reference resistor Rref is connected in series with the gas sensor 1 so as to form one arm of the Wheatstone bridge circuit 21 in the present embodiment. In this embodiment, the reference resistor Rref is formed to the same shape and dimensions from the same material as the gas sensor 1. Thereby, even when the gas sensor 1 changes its resistance due to variance of ambient temperature, influence of wind, heat conduction of the gas, or the like, the reference resistor Rref changes its resistance to nearly the same extent as the gas sensor 1 does, cancelling the fluctuation in the voltage at the connection point P1, thereby enabling to suppress the detection error.

In the embodiments described above, the gas detection apparatus enables to provide a large output voltage corresponding to the change in voltage at the connection point P1 between the heating resistor 2 and the load resistor R1 (or the reference resistor Rref), since the Wheatstone bridge circuit is configured of parallel combination of series circuits: one composed of the heating resistor 2 and the load resistor R1 (or the reference resistor Rref), and the other composed of the resistor R2, the variable resistor VR1 and the resistor R3. When the voltage level of the sampled output signal is large enough to be available in practical use, the pulsed heater voltage may be applied to the series circuit composed of the heating resistor 2 and the load resistor R1 (or the reference resistor Rref) without the need of the Wheatstone bridge circuit. In this case, the integrating circuit is configured to integrate the voltage at the connection point between the heating resistor 2 and the load resistor 1 (or the reference resistor Rref) for being fed to an amplification circuit. The amplification circuit amplifies the integrated voltage to be provided to the signal processing circuit 20 as the output signal of the gas sensing unit. By use of the output signal, the signal processing circuit 20 calculates the concentration of the flammable gas based on the calibration curve data stored in the internal memory.

As mentioned above, it is obvious that many widely different embodiments may be made in accordance with the technical concept of the present invention, and therefore the present invention should not be limited to the specific embodiments except as defined in the claims.

The invention claimed is:

1. A gas detection apparatus comprising:
   a gas sensing unit having
      a detection resistor heated by Joule heat in the presence of an electric current flowing therethrough and
      an igniter configured to ignite a flammable gas by a catalytic action as a result of being heated by the heat of said detection resistor;
   a load resistor connected in series to said detection resistor;
   a plurality of bridge resistors connected between both ends of a series circuit composed of said detection resistor and said load resistor to form a bridge circuit with the series circuit;
   a heater voltage application circuit configured to apply a pulsed heater voltage having a cycle shorter than a thermal time constant of said gas sensing unit across the series circuit composed of said detection resistor and said load resistor;
   a first integrating circuit unit composed of a CR integrating circuit including a resistor and a capacitor, and configured to integrate a voltage at a connection point between said detection resistor and said load resistor;
   a second integrating circuit unit composed of a CR integrating circuit including a resistor and a capacitor, and configured to integrate a voltage at a connection point between said bridge resistors;
   a differential amplification circuit unit configured to amplify a differential voltage between output voltages of both said integrating circuit units; and
   a gas detection circuit configured to provide an output signal of a magnitude corresponding to a concentration of the flammable gas from an output of said differential amplification circuit unit.

2. A gas detection apparatus as set forth in claim 1, wherein said gas detection circuit comprises
   a reference resistor which is formed to the same shape and dimensions from the same material as said detection resistor, and configured to be deactivated by the flammable gas.

3. The gas detection apparatus as set forth in claim 1, wherein said gas detection circuit comprises
   a sampling circuit unit configured to sample an output signal of the gas sensing unit at predetermined intervals for detecting the flammable gas based on the sampled output signal.

4. The gas detection apparatus as set forth in claim 2, wherein said gas detection circuit comprises
   a sampling circuit unit configured to sample an output signal of the gas sensing unit at predetermined intervals for detecting the flammable gas based on the sampled output signal.

* * * * *